United States Patent [19]

Weier

[11] 4,064,177

[45] Dec. 20, 1977

[54] 3-ALKOXY-D-HOMO-C-NOR-13α, 14α-GONA-1,3,5,(10),6,8-PENTAEN-17-ONE AND DERIVATIVES THEREOF

[75] Inventor: Richard M. Weier, Deerfield, Ill.

[73] Assignee: G. D. Searle & Co., Chicago, Ill.

[21] Appl. No.: 786,303

[22] Filed: Apr. 11, 1977

[51] Int. Cl.$^2$ .................... C07C 49/76; C07C 49/82; C07C 49/84
[52] U.S. Cl. ...................... 260/590 FB; 260/611 F; 260/617 F; 424/331; 424/340; 424/346
[58] Field of Search ......... 260/586 E, 590 FB, 611 F, 260/617 F

[56] References Cited

U.S. PATENT DOCUMENTS 3,228,951  1/1966  Johns et al. .................. 260/586 E

OTHER PUBLICATIONS

Neef et al., "Chem. Ber. 109", pp. 3025–3033, (1976).

*Primary Examiner*—Gerald A. Schwartz
*Attorney, Agent, or Firm*—Michael T. Murphy

[57] ABSTRACT

The present invention relates to 3-alkoxy-D-homo-C-nor-13α,14α-gona-1,3,5(10),6,8-pentaen-17-one and certain derivatives thereof. The compounds of this invention display valuable pharmacological activities, such as antispasmodic utility.

9 Claims, No Drawings

3-ALKOXY-D-HOMO-C-NOR-13 ALPHA, 14 ALPHA-GONA-1,3,5,(10),6,8-PENTAEN-17-ONE AND DERIVATIVES THEREOF

SUMMARY OF THE INVENTION

The present invention relates to a group of D-homo-C-nor steroids of the formula

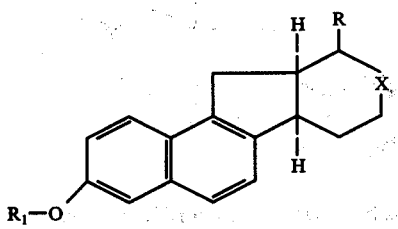

wherein R is hydrogen or alkyl containing 1 to 6 carbon atoms; $R_1$ is hydrogen or alkyl radical containing 1 to 6 carbon atoms and X is a carbonyl group or a group of the formula

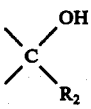

wherein $R_2$ is hydrogen, ethynyl or an alkyl containing 1 to 3 carbon atoms. The alkyl radicals containing 1–6 carbon atoms are exemplified by methyl, ethyl, propyl, butyl, pentyl, hexyl and the corresponding branched chain isomers.

An embodiment of this invention are compounds of the formula

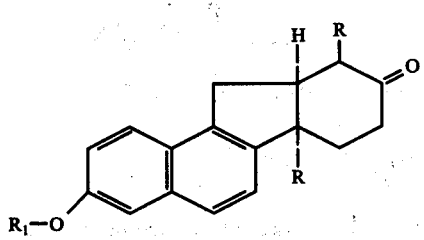

wherein R is hydrogen or alkyl containing 1 to 6 carbon atoms and $R_1$ is hydrogen or alkyl containing 1 to 6 carbon atoms.

Another embodiment of this invention are compounds of the formula

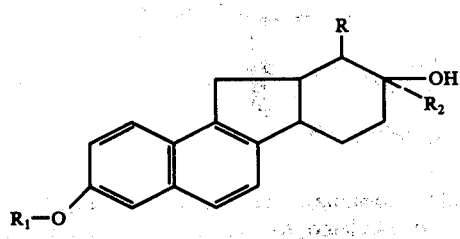

wherein R is hydrogen or alkyl containing 1 to 6 carbon atoms, $R_1$ is hydrogen or alkyl containing 1 to 6 carbon atoms and $R_2$ is hydrogen, ethynyl or alkyl containing 1 to 3 carbon atoms.

DETAILED DESCRIPTION OF THE INVENTION

The compounds of this invention are useful by reason of their valuable biological properties. In particular, they are antispasmodic.

The antispasmodic utility of the instant compounds is evident from the results of a standardized test for their capacity to antagonize the activity of bradykinin, prostaglandin $E_2$ ($PGE_2$) and/or acetylcholine. The procedure, carried out substantially as described by J. H. Sanner in Arch, Intern. Pharmacodynamic, 180, 46 (1969), is as follows: A female guinea pig weighing between 200 and 500 g is sacrificed by cervical dislocation, whereupon the ileum is quickly removed and a 2-cm segment thereof mounted in a 5-ml tissue bath containing modified Tyrode solution and adapted to record isotonic contractions. The Tyrode solution, at 37° C. and constantly bubbled with a mixture of 95% oxygen and 5% carbon dioxide (V/V), consists of 8.046 g of NaCl, 0.200 g of KCl, 0.32 g of $CaCl_2.2H_2O$, 0.107 g of $MgCl_2.6H_2O$, 1.000 g of $NaHCO_3$, 0.58 g of $NaH_2PO_4.H_2O$, 1.000 g of dextrose, and $H_2O$ q.s. 1 l. Doses of bradykinin, $PGE_2$, and acetylcholine necessary to induce approximately equal submaximal contractions are experimentally determined, whereupon two sets of three (one for each agonist at the predetermined dose) such contractions are recorded at 4-minute intervals as controls. The modified Tyrode solution is immediately replaced by a solution or suspension of test compound therein, at 37° and bubbled as before, following which three sets of contractions induced by the three agonists at the predetermined doses are recorded, beginning 4 minutes after the second control recording and continuing at 4-minute intervals thereafter. The first of these three sets serves only to maintain the dosage timing until the tissue is in equilibrium with the test compound. The last two sets are compared with the two control sets, and a compound is considered active vis-a-vis a given agonist if the mean contraction induced thereby in the presence of compound is not more than 25% of the mean control contraction for that agonist. The initial screening dose in this test is ordinarily 30 mcg per ml. The product 3-methoxy-D-homo-C-nor-13α,14α-gona-1,3,5(10),6,8-pentaen-17-one of this invention was active at this dose, while the product 17-hydroxy-3-methoxy-D-homo-C-nor-13α,14α-gona-1,3,5(10),6,8-pentaene was active at doses of 10 mcg per ml.

Those skilled in the art will recognize that observations of activity in standardized test for particular biological effects are fundamental to the development of valuable new drugs, both veterinary and human.

Compounds of the present invention are obtained by processes originating with compounds of the formula

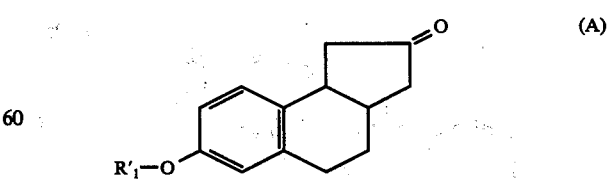

wherein $R_1'$ is an alkyl radical containing 1–6 carbon atoms. The starting materials are prepared according to the procedure set out by Juday et al, J. Med. Chem., 13, 314 (1970). These compounds are dehydrogenated with palladium metal catalyst in an appropriate inert solvent, such as toluene, xylene or p-cymene, under nitrogen. The inert solvents are preferred over benzene because the solution may be refluxed at higher temperatures than those possible with lower boiling solvents. The compounds formed are of the formula

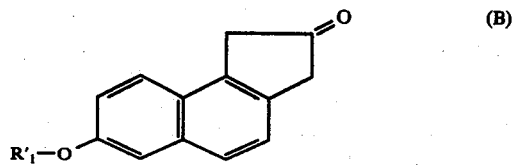
(B)

To a solution containing a compound of formula B in an anhydrous ether is added freshly dried and distilled pyrrolidine and anhydrous calcium chloride. The slurry is stirred under nitrogen at room temperature affording a compound of the formula

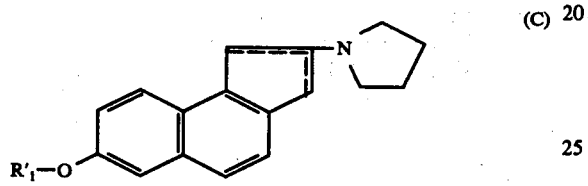
(C)

A compound of formula C is reacted with methyl vinyl ketone in benzene and then refluxed. A buffer solution is then added and reflux is continued. The product formed is of the formula

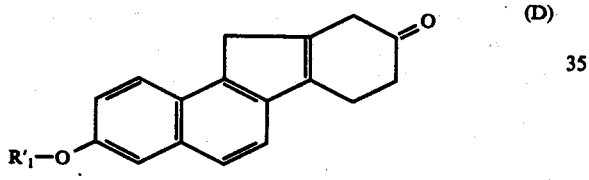
(D)

Compound D is catalytically hydrogenated to afford the compound of the present invention of the formula

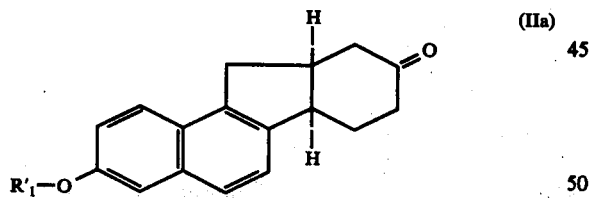
(IIa)

Compounds of formula IIa may further be chemically reduced to afford the corresponding compounds of the present invention of the formula

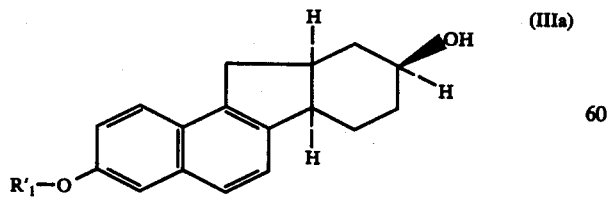
(IIIa)

Alternatively compounds of formula IIa may be used to produce compounds of formula II wherein R is an alkyl radical containing 1-6 carbon atoms. A compound of formula IIa is added to a solution which has been prepared by mixing diisopropyl amine in anhydrous ether and n-butyl lithium in hexane. An appropriate aldehyde containing 1-6 carbon atoms is added to the solution affording the corresponding compound of the formula

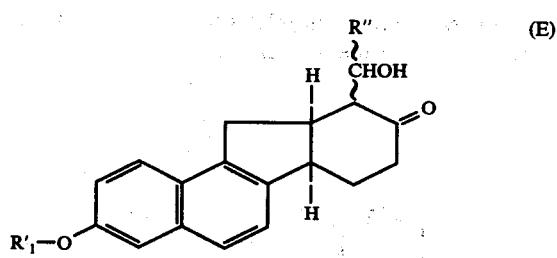
(E)

wherein R" is hydrogen or alkyl radical containing 1-5 carbon atoms.

Compound E is added to an acetone: water (3:1) solution which has been previously adjusted to pH 1.5-2.0 with 0.1N HCl. The compound formed is

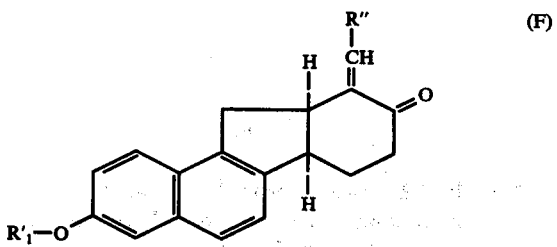
(F)

Compound F is catalytically hydrogenated to afford the compound of the present invention of the formula

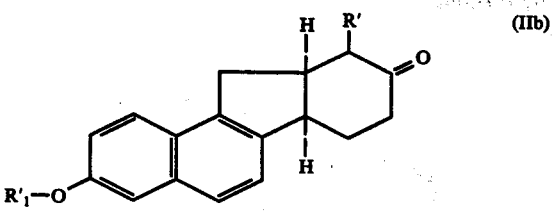
(IIb)

wherein R' is an alkyl radical containing 1-6 carbon atoms.

Compounds of formula IIb may further be chemically reduced, under nitrogen, to afford the corresponding compounds of the present invention of the formula

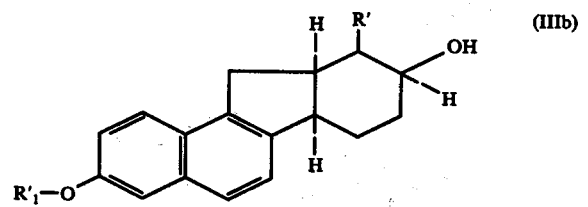
(IIIb)

Compounds of formula II (which include IIa and IIb above) may be alkylated to produce compounds of formula III wherein $R_2$ is an alkyl radical containing 1-3 carbon atoms. A compound of formula II is added to an ether solution containing alkyl lithium, wherein alkyl contains 1-3 carbon atoms, affording compounds of the present invention of the formula

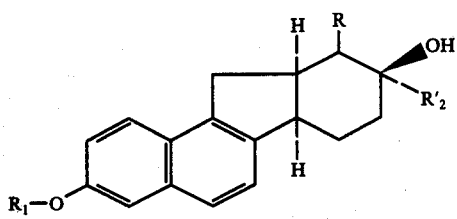

wherein $R_2'$ is an alkyl radical containing 1-3 carbon atoms.

When sodium acetylide is substituted for the alkyl lithium above there is produced compounds of the formula

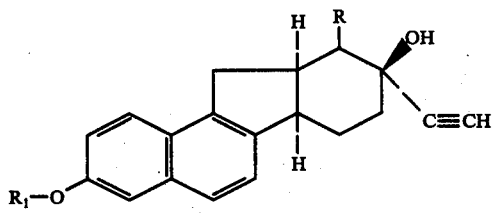

When compounds of the formula

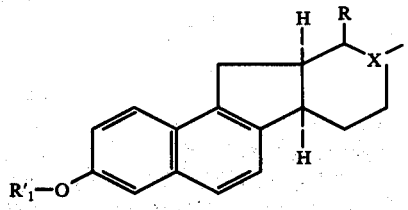

wherein R is hydrogen or alkyl containing 1 to 6 carbon atoms; X' is a carbonyl group or group of the formula

and $R_1'$ is an alkyl radical containing 1-6 carbon atoms are refluxed with 1:1 48% hydrobromic acid - glacial acetic acid the corresponding 3-hydroxy compounds are produced.

The following examples describe in detail the preparations of compounds illustrative of the present invention. It will be apparent to those skilled in the art that many modifications, both of materials and methods, may be practiced without departing from the purpose and intent of this disclosure. Throughout the examples hereinafter set forth, temperatures are given in degrees Centigrade (° C) and relative amounts in parts by weight, except as otherwise noted.

EXAMPLE 1

A slurry of 0.72 parts 10% Pd/C in 86 parts p-cymene was azeotropically dried by distilling off 20 parts of the solvent. 1.25 Parts 3,3a,4,5-tetrahydro-7-methoxy-2H-benz[e]inden-2-one, having the formula

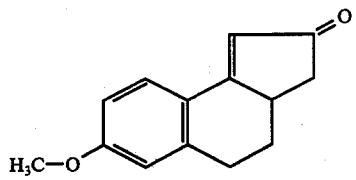

is added to the slurry and the reaction vessel is purged with nitrogen for 30 minutes. The mixture is refluxed for 6 hours.

The mixture is cooled, filtered through Super Cel and the filter cake is washed with toluene. The filtrate is concentrated by evaporation, and the p-cymene is removed by careful distillation on the vacuum pump. The light tan solid which is produced is recrystallized from methanol to afford 1,3-dihydro-7-methoxy-2H-benz[e]-inden-2-one which melts at 138°-140° C. This product is represented by the formula

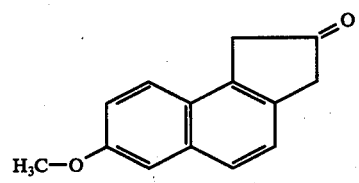

EXAMPLE 2

To a solution of 11.44 parts 1,3-dihydro-7-methoxy-2H-benz[e]inden-2-one in 266 parts tetrahydrofuran is added 12.8 parts freshly dried and distilled pyrrolidine and 22 parts anhydrous calcium chloride granules. This slurry is stirred under nitrogen at room temperature for 18 hours. The resulting green reaction solution is diluted with tetrahydrofuran and filtered through Super Cel. The filter cake is thoroughly washed. The filtrate is stripped in vacuo to give a green solid. This material is transferred to a sintered glass funnel using ethyl ether, and the material is washed on the filter three more times with ethyl ether. The solid was dried in air to yield a mixture of 1-(3a,4,5,9b-tetrahydro-7-methoxy-3H-benz[e]inden-2-yl)pyrrolidine and 1-(3a,4,5,9b-tetrahydro-7-methoxy-1H-benz[e]inden-2-yl)pyrrolidine which melts at 159° to 162° C. This mixture is represented by the formula

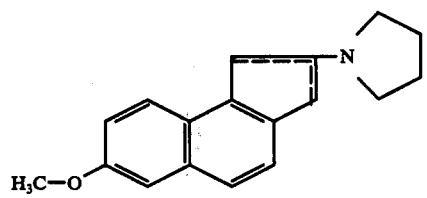

EXAMPLE 3

A slurry of 2.17 parts of the mixture prepared in Example 2 in 78.7 parts benzene is stirred at room temperature under nitrogen for 15 minutes. 0.52 Part methyl vinyl ketone is added to the slurry. The solution is stirred at room temperature for 1 hour and then refluxed for 17 hours. 10 Parts of buffer solution of sodium acetate; acetic acid; water (1:2:2, w:v:v) is then added and the mixture is refluxed for 2 hours.

50 Parts water is added to the resultant mixture and the layers are separated. The benzene layer is washed twice with water, twice with 5% potassium bicarbonate, and dried over anhydrous sodium sulfate. Evaporation of the benzene in vacuo gives a soft brown solid which is chromatographed on silica, using benzene. Recrystallication of this material from benzene affords 3-methoxy-D-homo-C-nor-gona-1,3,5(10), 6,8,13(14)-hexaen-17-one which melts at 176°–181° C. This compound is represented by the formula

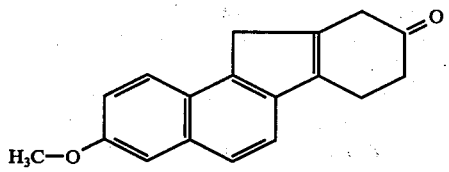

EXAMPLE 4

0.704 Part of the 3-methoxy-D-homo-C-nor-gona-1,3,5(10),6,8,13(14)-hexaen-17-one in III parts tetrahydrofuran is hydrogenated at atmospheric pressure and ambient temperature using 0.14 part 10% Pd/C as catalyst. The theoretical uptake of hydrogen occurs in about 2 hours. The catalyst is filtered out and the filtrate is concentrated to dryness by evaporation to give a colorless solid. The solid is crystallized under ethyl ether and then the supernatant ethyl ether is decanted. The crystalline residue is recrystallized from ethyl ether to afford 3-methoxy-D-homo-C-nor-13α,14α-gona-1,3,5(10),6,8-pentaen-17-one which melts at 90°–92° C. This product is represented by the formula

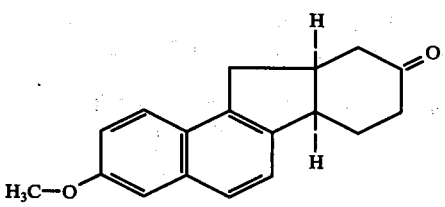

EXAMPLE 5

A solution of 0.67 part 3-methoxy-D-homo-C-nor-13α,14α-gona-1,3,5(10),6,8,-pentaen-17-one in 7.1 parts tetrahydrofuran is added to a cold (0° C), stirred solution of 1.47 parts lithium tri-t-butoxy aluminum hydride in 44.4 parts tetrahydrofuran under nitrogen. The reaction is allowed to come to room temperature and is stirred for 3 hours. It is again cooled to 0° C and excess hydride reagent is destroyed with 5.0 parts 20% acetic acid in water. The reaction is stripped in vacuo, the residue is diluted with water and then extracted three times with methylene chloride. The extractions are combined and dried over anhydrous sodium sulfate. The solution is evaporated to dryness and the colorless residue is subjected to low pressure liquid phase chromatography on silica usuing 3% ethyl acetate in benzene as the eluant. The crystalline solid which is recovered is recrystallized from benzene and then dried at 80° C. on a thermo pump. The final product is 17β-hydroxy-3-methoxy-D-homo-C-nor-13α, 14α-gona-1,3,5(10),6,8-pentaene which melts at 141°–143° C and is represented by the formula

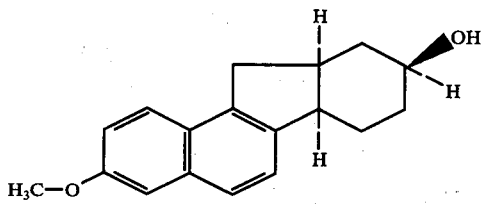

EXAMPLE 6

A stirred solution of 1.01 parts diisopropyl amine in 44.4 parts anhydrous tetrahydrofuran is cooled to -78° C while maintaining a nitrogen blanket over the surface of the reaction solution. A solution containing 4.2 parts (by volume) of 2.4 M n-butyl lithium in hexane and 8.9 parts tetrahydrofuran is added to the above amine solution. The resultant solution is stirred in the cold for 10 minutes. A solution of 2.66 parts 3-methoxy-D-homo-C-nor-13α, 14α-gona-1,3,5(10),6,8-pentaen-17-one in 13.3 parts tetrahydrofuran is then added dropwise over a 5 minute period. At this time, gaseous formaldehyde at exactly 150° C, is conducted into the reaction mixture using nitrogen as a carrier gas. When no more paraformaldehyde remains the reaction mixture is allowed to come to 0° C. and is then quenched with 10 parts water.

The reaction mixture is concentrated in vacuo. The residue is dissolved in methylene chloride and the organic layer is washed twice with water. After drying over anhydrous sodium sulfate and solvent is removed in vacuo and the residue is subjected to low pressure liquid chromatrography on neutral silica. The product is taken up in ethyl acetate, and then Skellysolve B is added until the product recrystallizes. The recrystallized product is a mixture of 17aα-hydroxymethyl-3-methoxy-D-homo-C-nor-13α,14α-gona-1,3,5(10),6,8-pentaen-17-one and 17aβ-hydroxymethyl-3-methoxy-D-homo-C-nor-13α,14α-gona-1,3,5(10),6,8-pentaen-17-one which is represented by the figure

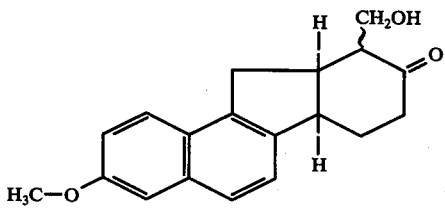

EXAMPLE 7

2.0 Parts 17a-hydroxymethyl-3-methoxy-D-homo-C-nor-13α,14α-gona-1,3,5(10),6,8-pentaen-17-one is added to a 133 parts (by volume) solution of acetone:water (3 parts volume: 1 part volume) that has been previously adjusted to pH 1.5–2.0 with 0.1 N HCl. After stirring for one hour at room temperature, the reaction solution is concentrated in vacuo to give a gummy white precipitate. The crude product is dissolved in 53.4 parts methylene chloride and washed successively with water, 5% sodium bicarbonate and water. The organic solution is then dried over anhydrous sodium sulfate. Removal of the solvent in vacuo gives a colorless residue that is purified by low pressure liquid chromatography over neutral silica, eluting with mixtures of ethyl acetate and benzene. The product is taken up in ethyl acetate, and the Skellysolve B is added until the product recrystallizes. The resulting product is 3-methoxy-17a-methylene-D-homo-C-nor-13α,14α-gona-1,3,5(10),6,8-pentaen-17-one which is represented by the figure

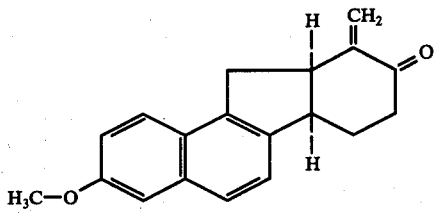

EXAMPLE 8

A solution of 1.0 part 3-methoxy-17a-methylene-D-homo-C-nor-13α,14α-gona-1,3,5(10),6,8-pentaen-17-one in 44.4 parts tetrahydrofuran is hydrogenated at atmospheric pressure and ambient temperature using 0.09 parts pre-reduced 5% Pd/C as catalyst. When hydrogen uptake is complete the catalyst is filtered and the filtrate is stripped in vacuo to give a colorless oil. The product is purified by low pressure liquid phase chromatography over natural silica, eluting with mixtures of ethyl acetate and benzene. The product is taken up in ethyl acetate, and then Skellysolve B is added until the product recrystallizes. The resulting product is 3-methoxy-17aβ-methyl-D-homo-C-nor-13α,14α-gona-1,3,5(10),6,8-pentaen-17 -one which is represented by the figure

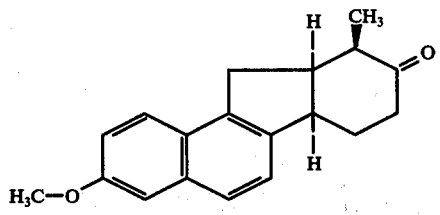

EXAMPLE 9

To a stirred, cold (0° C) solution of 2.0 parts lithium tri-t-butoxy aluminum hydride in 53.3 parts tetrahydrofuran under nitrogen is added a solution of 1.0 part 3-methoxy-17aβ-methyl-D-homo-C-nor-13α,14α-gona-1,3,5(10),6,8-pentaen-17-one in 8.9 parts anhydrous tetrahydrofuran dropwise over a 5 minute period. The ice bath is removed and the reaction is stirred at room temperature for 4.5 hours. The reaction is again cooled to 0° C and excess hydride reagent is destroyed by adding 15.0 parts 20% acetic acid in water. The resulting mixture is concentrated in vacuo to give a mixture of white gummy material in aqueous acetic acid. The organic material is dissolved in methylene chloride and the layers are separated. The aqueous layer is washed twice more with methylene chloride. The combined methylene chloride washings are washed once with water, four times with 5% potassium bicarbonate, once more with water, and then dried over anhydrous sodium sulfate.

The product is purified by low pressure liquid phase chromatography over neutral silica eluting with mixture of ethyl acetate and benzene. The product is taken up in ethyl acetate, and then Skellysolve B is added until the product recrystallizes. The resulting product is 17β-hydroxy-3-methoxy-17aβ-methyl-D-homo-C-nor-13α,-14α-gona-1,3,5(10),6,8-pentaene which is represented by the figure

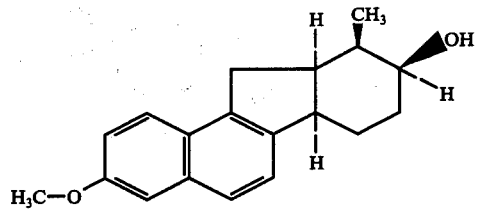

EXAMPLE 10

To a stirred, cold (0° C) solution of 7.7 parts (by volume) 1.3 M ethereal methyl lithium in 21.1 parts tetrahydrofuran under nitrogen is added a solution of 2.8 parts 3-methoxy-17aβ-methyl-D-homo-C-nor-13α,-14α-gona-1,3,5(10),6,8-pentaen-17-one in 16.8 parts anhydrous tetrahydrofuran. The addition is carried out in a dropwise manner over a 10 minute period. After addition, the ice bath is removed and the reaction is allowed to stir at room temperature for 4 hours.

The reaction solution is again cooled to 10° C and 10.0 parts water is added. The solution is concentrated in vacuo giving a gummy material suspended in water. Methylene chloride is added to dissolve the organic material and the layers were separated. The aqueous layer is washed twice with methylene chloride. The combined organic layers are washed twice with water and dried over anhydrous sodium sulfate. The solvent is removed in vacuo to yield to colorless oil residue.

The product is purified by low pressure liquid phase chromatography over neutral silica, eluting with mixtures of ethyl acetate and benzene. The product is taken up in ethyl acetate, and then Skellysolve B is added until the product recrystallizes. The resulting product is 17β-hydroxy-3-methoxy-17α17aβ-dimethyl-D-homo-C-nor-13α,14α-gona-1,3,5(10),6,8-pentaene which is represented by the figure

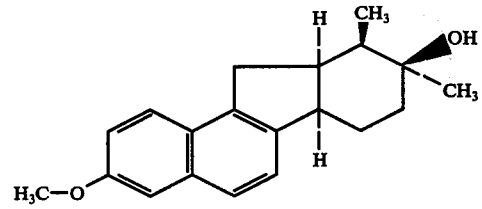

EXAMPLE 11

When an equivalent amount of sodium acetylide-ethylene diamine is substituted for the etheral methyl lithium in Example 10, and the procedure therein is substantially repeated, there is obtained 17α-ethynyl-17β-hydroxy-3-methoxy-17aβ-methyl-D-homo-C-nor-13α,14α-gona-1,3,5(10),6,8-pentaene, which is represented by the figure

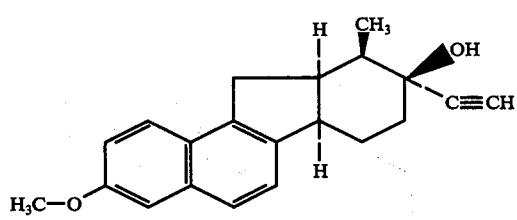

What is claimed is:

1. A compound of the formula

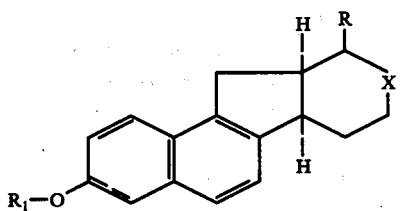

wherein R is hydrogen or alkyl contaning 1 to 6 carbon atoms; $R_1$ is hydrogen or alkyl containing 1 to 6 carbon atoms and X is a carbonyl group or a group of the formula

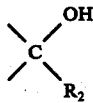

wherein $R_2$ is hydrogen, ethynyl or alkyl containing 1 to 3 carbon atoms.

2. A compound according to claim 1 of the formula

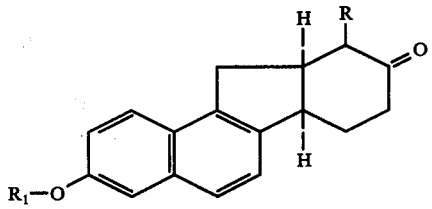

wherein R is hydrogen or alkyl containing 1 to 6 carbon atoms and $R_1$ is hydrogen or alkyl containing 1 to 6 carbon atoms.

3. The compound according to claim 1 which is 3-methoxy-17aβ-methyl-D-homo-C-nor-13α,14α-gona-1,3,5(10),6,8-pentaen-17-one.

4. The compound according to claim 1 which is 3-methoxy-D-homo-C-nor-13α,14α-gona-1,3,5(10),6,8-pentaen-17-one.

5. A compound according to claim 1 of the formula

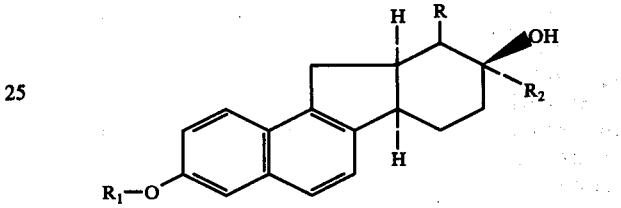

wherein R is hydrogen or alkyl containing 1 to 6 carbon atoms; $R_1$ is hydrogen or alkyl containing 1 to 6 carbon atoms and $R_2$ is hydrogen, ethynyl or alkyl containing 1 to 3 carbon atoms.

6. The compound according to claim 1 which is 17β-hydroxy-3-methoxy-D-homo-C-nor-13α,14α-gona-1,3,5(10),6,8-pentaene.

7. The compound according to claim 1 which is 17β-hydroxy-3-methoxy-17aβ-methyl-D-homo-C-nor-13α,14α-gona-1,3,5(10),6,8-pentaene.

8. The compound according to claim 1 which is 17β-hydroxy-3-methoxy-17α,17aβ-dimethyl-D-homo-C-nor-13α,14α-gona-1,3,5(10),6,8-pentaene.

9. The compound according to claim 1 which is 17α-ethynyl-17β-hydroxy-3-methoxy-17aβ-methyl-D-homo-C-nor-13α,14α-gona-1,3,5(10),6,8-pentaene.

* * * * *